US00PP17368P2

(12) United States Plant Patent
Lemon

(10) Patent No.: US PP17,368 P2
(45) Date of Patent: Jan. 16, 2007

(54) ***GERANIUM* PLANT NAMED 'GLOBAL ORCHID'**

(50) Latin Name: *Pelargonium peltatum*
Varietal Denomination: Global Orchid

(75) Inventor: David G. Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 10 days.

(21) Appl. No.: 11/177,066

(22) Filed: Jul. 8, 2005

(51) Int. Cl.
*A01H 5/00* (2006.01)

(52) U.S. Cl. ..... Plt./332
(58) Field of Classification Search ..... Plt./332
See application file for complete search history.

*Primary Examiner*—Kent Bell
*Assistant Examiner*—Annette H Para
(74) *Attorney, Agent, or Firm*—The Webb Law Firm

(57) ABSTRACT

'Global Orchid' is a new variety of *geranium* having free flowering, good heat tolerance, and deeply colored lavender flowers.

1 Drawing Sheet

Botanical classication: *Pelargonium peltatum.*
Varietal denomination: 'Global Orchid'.

BACKGROUND OF THE INVENTION

The present invention comprises a new and distinct cultivar of *Pelargonium peltatum* known by the varietal name 'Global Orchid'. The new variety was discovered in Lompoc, Calif. The new variety is a result of cross breeding 'Amethyst' (female parent) (unpatented) and seedling 'Single Pink' (male parent) (unpatented). The purpose of the breeding program was to develop compact Ivy *geraniums* for use in 4" pots and small baskets. The new variety exhibits a deeper flower color and better heat tolerance when compared to its female parent. 'Global Orchid' also is free flowering like its male parent, but exhibits double flowers and a deep lavender color. The free flowering and good heat tolerance of 'Global Orchid' helps to distinguish it from other varieties known to the breeder. The new variety was first asexually reproduced by cuttings in Connellsville, Pa. The new variety has been trial and field tested and has been found to retain its distinctive characteristics and remain true to type through successive propagations.

The new variety was grown in a 4" pot in a glass greenhouse in Connellsville, Pa. using full light, 16° C. night temperature and 20° C. day temperature and grown in a soilless media with constant fertilizer at 200–250 ppm nitrogen and potassium. The new variety exhibits rooting at 7–10 days under optimal conditions and has a response time of eleven weeks from a rooted cutting to flowering.

DESCRIPTION OF THE DRAWING

The accompanying photographic drawing illustrates the new variety, with the color being as nearly true as is possible with color illustrations of this type.

DESCRIPTION OF THE PLANT

Figure 1:
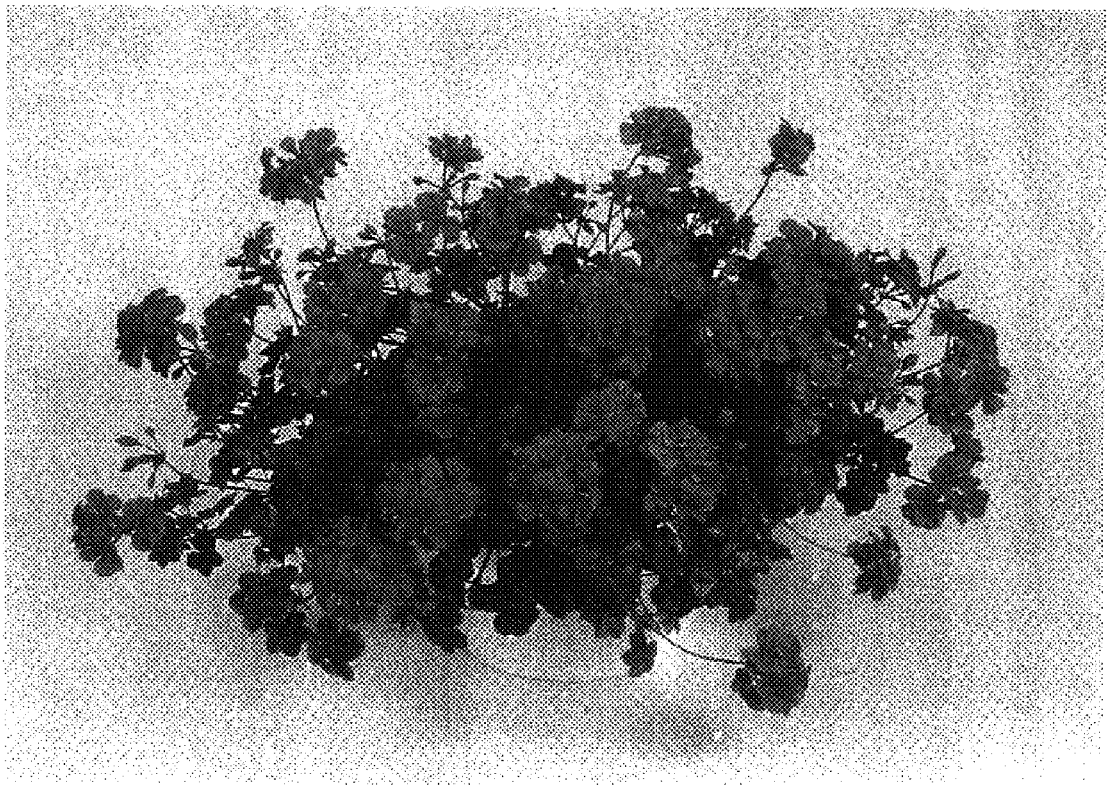

The following detailed description sets forth the characteristics of the new cultivar. The data which defines these characteristics were collected by asexual reproductions carried out in Connellsville, Pa. The new variety was eight weeks old from a rooted cutting when described. The color readings were taken indoors under 200–220 foot candles of cool white fluorescent light. Color references are primarily to the 1966 R.H.S. Colour Chart of The Royal Horticultural Society of London.

PLANT

Market class: Ivy.
Time to initiate roots: About 7–10 days at about 23° C.
Time to develop roots: About 21 days at about 23° C.
Time to produce a finished flowering plant from a rooted cutting: Approximately 11 weeks in a 10" basket.
Rooting habit: Good, normal.
Form: Trailing and spreading.
Height from media surface to top of foliage: 9.0–12.5 cm.
Height from media surface to top of flowers: 19 cm.
Plant diameter: 24.0 cm.
Vigor: 3 on a scale of 5.
Strength: No artificial support is needed.
Branching habit: Free branching.
Stem:
- *Main stem length.*—34.0–36.0 cm.
- *Diameter.*—0.35–0.45 cm.
- *Color.*—Yellow-Green Group 144A.
- *Texture.*—Leathery texture.
- *Pubescence.*—Light to none.
- *Internode length.*—4.5–6.8 cm.

Lateral branches:
- *Length.*—Primary: 7.0–23.0 cm. Secondary: 6.5–9.0 cm.
- *Diameter.*—Primary: 0.35–0.4 cm. Secondary: 0.3–0.35 cm.
- *Internode length.*—2.5–6.0 cm.
- *Texture.*—Leathery.
- *Pubescence.*—Light.
- *Color.*—Yellow-Green Group 144A.

Foliage:
- *Arrangement.*—Opposite; alternate.
- *Stipules.*—Size: 0.7 cm. high by 1.4 cm. wide. Color: Yellow-Green Group 144A.
- *Zone.*—Not present.
- *Size of leaf.*—Length: 5.3–7.3 cm. Width: 4.2–6.2 cm.
- *Shape of leaf.*—Reniform with a cordate base.
- *Shape of apex.*—Reniform.
- *Shape of base.*—Cordate.
- *Texture.*—Leathery.
- *Aspect.*—Leaves have a very slight slope increasing from point of connection toward the margin.

*Margin type.*—Pedately lobed.
*Pubescence.*—Upper surface: Light. Lower surface: Light.
*Color.*—Young leaves: Upper surface: Green Group 137A. Lower surface: Green Group 137C. Mature leaves: Upper surface: Green Group 137A. Lower surface: Green Group 137C.
*Petiole.*—Length: 2.7–4.2 cm. Diameter: 1.5–2.0 mm. Color: Yellow-Green Group 144A.
*Veins.*—Venation type: Palmate. Color: Upper surface: Green Group 137B. Lower surface: Yellow-Green Group 144A.

INFLORESCENCE

Bud:
*Stage of development when bud characteristics determined.*—Bud shows color at side but sepals are not parting at the tips.
*Shape of cluster.*—Elongated and elliptical cluster.
*Diameter of cluster.*—2.8–4.8 cm.
*Number of buds per cluster.*—5–7.
*Shape of individual bud.*—Ellipse.
*Length of individual bud.*—1.2–1.4 cm.
*Width of individual bud.*—0.6–0.8 cm.
Natural flowering season at specified location(s): Year round horticultural greenhouse crop.
Blooming habit: Continuous and free flowering.
Umbel diameter: 7.0–9.8 cm.
Umbel depth: 4.0–5.2 cm.
Borne: Umbel, flowers on pedicel, pedicel on peduncle.
Inflorescence position: Above foliage.
Number of inflorescences per lateral branch: 1–2.
Lastingness of an individual flower: 10–14 days.
Florets:
*Form.*—Flat and slightly cupped. As flowers mature, the florets gradually become more open/flat.
*Number per umbel.*—4–6.
*Diameter.*—4.2–4.7 cm.
*Depth.*—1.9–2.2 cm.
Petals:
*Color.*—The top two–three petals of the floret have a blotch that is not present in the bottom petals. Upper surface: The top two or three petals are Red-Purple Group 74C. The lower half of the petal begins a blotch of Red-Purple Group 61A. The venation leading up to and around the blotch is Purple Group 79A. Above the blotch the venation fades to Red-Purple Group 74A. At the point of connection the coloring fades to White Group 155D. The bottom petals are Red-Purple Group 74C with Red-Purple Group 74A venation. The point of connection then immediately fades to a White Group 155D. Lower surface: The top two or three petals begin as Red-Purple Group 72C and fade to Red-Purple Group 73C as it approaches the center of the petal. The dark Red-Purple Group 71B venation is present on the lower surface of the petals. At the base, the connection point is White Group 155D. The bottom petals are Red-Purple Group 72C and fade slowly to Red-Purple Group 73B as it approaches the center of the petal. The venation present is Red-Purple Group 71D with the connection point fading immediately to White Group 155D.
*Shape.*—Inverted teardrop.
*Length.*—2.3–2.9 cm.
*Width.*—1.5–1.9 cm.
*Apex shape.*—Smooth and rounded.
*Base shape.*—Tapered to a point.
*Margin.*—Entire; smooth.
*Number per floret.*—6–8.
*Texture.*—Smooth.
*Tonality from a distance.*—Vibrant pink flowers with dark purple-red eyes staring back atop of mounding medium green foliage.
Petaloids:
*Quantity.*—0–4 per floret.
*Shape.*—Splits in a two-pronged unit or are tubular.
*Color* (*upper and lower surface*).—Tubular petals have an inner surface as Red-Purple Group 71B and outer surface of Red-Purple Group 73B and fade to White Group 155D near the point where it connects to the pedicel. Split florets have an upper surface Red-Purple Group 74C and fade to White Group 155D at the connection point. The undersides are Red-Purple Group 72C and fade to White Group 155D.
*Length.*—0.8–1.9 cm.
*Width.*—0.3–1.2 cm.
Pedicel:
*Length.*—2.1–2.6 cm.
*Diameter.*—0.13–0.20 cm.
*Color.*—Yellow-Green Group 144A pedicels with varying intensities of Greyed-Purple Group 185A on the upper sides of the pedicel with the deepest intensity occurring near the pedicel-peduncle point of connection.
Peduncle:
*Length.*—9.1–11.9 cm.
*Diameter.*—0.2–0.35 cm.
*Texture.*—A slightly rough leather texture with a slight to moderate amount of pubescence.
Color: Yellow-Green Group 144A.
Sepal:
*Number.*—5.
*Pubescence.*—Long but sparse.
*Shape.*—Lanceolate.
*Width.*—0.3–0.5 cm.
*Length.*—1.4–1.5 cm.
Fragrance: No unusual fragrance.
Disease resistance: None observed.
Temperature tolerance: None observed.
Drought tolerance: None observed.

REPRODUCTIVE ORGANS

Stamens:
*Number* (*per flower*).—7–9.
*Filament.*—Length: 0.8–1.1 cm. Color: White Group 155D with the tip being Red-Purple Group 66A.
*Anthers.*—Shape: Oval-like with a slight curve. Length: 0.2–0.3 cm. Color: Grey-Purple Group 187B.
*Pollen.*—Color: Greyed-Orange Group 169A. Amount: Plentiful.
Pistils:
*Number.*—1.
*Length.*—1.0 cm.
*Style.*—Length: 0.5 cm. Color: Red Group 36D.
*Stigma.*—Shape: Style splits and radiates into 5 parts. Color: Red Group 46A. Size: 0.2 cm. high.
*Ovaries.*—Position: Superior. Pubescence: Present. Length: 0.3 cm. Width: 0.2 cm. Color: Yellow-Green Group 145B.

I claim:

1. A new and distinct variety of *geranium* named 'Global Orchid' as herein described and illustrated.

* * * * *